United States Patent
Mahrouche et al.

(10) Patent No.: US 10,788,244 B2
(45) Date of Patent: Sep. 29, 2020

(54) RECOVERY SYSTEM FOR N20

(71) Applicant: Medtronic CryoCath LP, Toronto (CA)

(72) Inventors: Rachid Mahrouche, La Salle (CA); Eric Monger, Beloeil (CA); Vladimir Tzonev, Kirkland (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 429 days.

(21) Appl. No.: 15/012,341

(22) Filed: Feb. 1, 2016

(65) Prior Publication Data
US 2017/0219261 A1 Aug. 3, 2017

(51) Int. Cl.
*A61B 18/02* (2006.01)
*F25B 45/00* (2006.01)
(Continued)

(52) U.S. Cl.
CPC .............. *F25B 45/00* (2013.01); *A61B 18/02* (2013.01); *A61B 18/0218* (2013.01);
(Continued)

(58) Field of Classification Search
CPC .......... F25D 16/00; F25D 17/00; F25D 3/005; F25D 17/02; A61B 18/02; A61B 18/0218;
(Continued)

(56) References Cited

U.S. PATENT DOCUMENTS

| 4,336,691 A * | 6/1982 | Burstein | ............ A61B 18/0218 62/51.1 |
| 5,230,224 A * | 7/1993 | Ricketts | .................. F25B 45/00 62/292 |

(Continued)

FOREIGN PATENT DOCUMENTS

| CN | 1080388 A | 1/1994 |
| CN | 102971593 A | 3/2013 |

(Continued)

OTHER PUBLICATIONS

International Search Report and Written Opinion dated Apr. 26, 2017, for corresponding International Application No. PCT/CA2017/050074; International Filing Date: Jan. 25, 2017 consisting of 9 pages.

(Continued)

*Primary Examiner* — Thomas A Giuliani
*Assistant Examiner* — Christine A Dedoulis
(74) *Attorney, Agent, or Firm* — Christopher & Weisberg, P.A.

(57) ABSTRACT

A system for the recovery of expanded refrigerant from a cryotreatment system for storage and disposal may generally include first fluid flow path having a first compressor and a fluid recovery reservoir, and a closed-loop second fluid flow path having a thermal exchange device that is in thermal communication with the fluid recovery reservoir, a second compressor, and a condenser. The first fluid flow path may include a primary refrigerant from a cryotreatment system and the closed-loop second fluid flow path may contain a secondary refrigerant for cooling the primary refrigerant within the fluid recovery reservoir. The refrigerant recovery conduit may be in fluid communication with both the cryotreatment system and a medical facility scavenging system. The refrigerant recovery conduit and the cryotreatment system may be located within the same cryotreatment console.

1 Claim, 4 Drawing Sheets

(51) Int. Cl.
*A61B 18/12* (2006.01)
*A61B 90/00* (2016.01)
*A61B 18/00* (2006.01)
*A61F 7/00* (2006.01)

(52) U.S. Cl.
CPC ....... *A61B 18/12* (2013.01); *A61B 2018/0022* (2013.01); *A61B 2018/00101* (2013.01); *A61B 2018/00351* (2013.01); *A61B 2018/00577* (2013.01); *A61B 2018/00648* (2013.01); *A61B 2018/00791* (2013.01); *A61B 2018/00863* (2013.01); *A61B 2018/00898* (2013.01); *A61B 2018/00994* (2013.01); *A61B 2018/0262* (2013.01); *A61B 2090/063* (2016.02); *A61B 2090/064* (2016.02); *A61B 2218/007* (2013.01); *A61F 2007/0056* (2013.01); *F25B 2345/002* (2013.01)

(58) Field of Classification Search
CPC ........ A61B 2018/0262; A61B 18/0206; A61B 2018/0212; A61B 2018/0293; F25B 45/00; F25B 2400/05; F25B 2345/002; F25B 41/00; F25B 40/02
USPC .......................................................... 606/20
See application file for complete search history.

(56) References Cited

U.S. PATENT DOCUMENTS

| | | | | |
|---|---|---|---|---|
| 5,916,212 | A * | 6/1999 | Baust | A61B 18/02 606/22 |
| 6,237,355 | B1 * | 5/2001 | Li | A61B 18/02 62/114 |
| 6,306,129 | B1 * | 10/2001 | Little | A61B 18/02 128/DIG. 27 |
| 6,319,248 | B1 * | 11/2001 | Nahon | A61B 18/0218 604/523 |
| 6,468,268 | B1 * | 10/2002 | Abboud | A61B 18/02 606/20 |
| 6,530,234 | B1 * | 3/2003 | Dobak, III | A61B 18/02 62/52.1 |
| 2001/0007951 | A1 * | 7/2001 | Dobak, III | A61F 7/12 607/106 |
| 2007/0277550 | A1 * | 12/2007 | Li | A61B 18/02 62/612 |
| 2010/0057064 | A1 * | 3/2010 | Baust | A61B 18/02 606/21 |
| 2011/0054453 | A1 * | 3/2011 | Lalonde | A61B 18/02 606/23 |
| 2014/0207131 | A1 * | 7/2014 | Harmouche | A61B 18/02 606/22 |
| 2014/0276698 | A1 * | 9/2014 | Wittenberger | A61B 18/1492 606/21 |
| 2014/0330197 | A1 * | 11/2014 | Fontaine | A61M 11/04 604/23 |
| 2015/0345860 | A1 | 12/2015 | Rillo Millan et al. | |

FOREIGN PATENT DOCUMENTS

| | | |
|---|---|---|
| CN | 103987346 A | 8/2014 |
| GB | 1371797 | 10/1974 |
| GB | 1371797 A | 10/1974 |

OTHER PUBLICATIONS

Supplementary Partial European Search Report for Application No. EP 17746663, dated Jul. 23, 2019, Consisting of 4 pages.

European Patent Office, Supplementary European Search Report, dated Jul. 23, 2019 for corresponding EP Application No. 17 74 6663, 11 pages.

China National Intellectual Property Administration, Chinese Office Action and Search Report, dated May 19, 2020 for corresponding CN Application No. 201780005321.2, consisting of 16 pages.

* cited by examiner

US 10,788,244 B2

RECOVERY SYSTEM FOR N2O

CROSS-REFERENCE TO RELATED APPLICATION n/a

STATEMENT REGARDING FEDERALLY SPONSORED RESEARCH OR DEVELOPMENT n/a

TECHNICAL FIELD

The present invention relates to a method and system for the recovery of expanded refrigerant from a cryotreatment system for storage and disposal.

BACKGROUND

Cryotherapy includes variety of techniques used to treat and/or map tissue, and is commonly used for procedures involving cardiac tissue. Certain types of cryotherapy, such as cryoablation, involve the use of pressurized refrigerant, which is allowed to expand within, and thereby cool tissue adjacent to, the distal portion of the treatment device. The pressurized refrigerant is typically stored in a pressurized tank or cylinder in the console of the system. Although the tank is easily removed and replaced when the refrigerant source runs out, it would be more economical to refill the tank with a new supply of refrigerant. Additionally, the pressurized tanks are considered to be Dangerous Goods, and it would therefore be desirable to reduce the amount of transport, handling, and storage of refrigerant tanks used for cryotherapy procedures.

Many medical facilities, especially hospitals, include a native or in-facility, integrated source of nitrous oxide ($N_2O$), which is commonly used as an anesthetic. Nitrous oxide may also be used as a refrigerant in cryotherapy systems. The expanded or used nitrous oxide must be scavenged from the system, but many medical facilities do not have adequate scavenging systems for recapture, storage, and disposal of nitrous oxide vapor.

It is therefore desirable to provide a system and method for recapturing or scavenging used refrigerant vapor for storage and disposal. It is further desired that the system be contained within a cryotreatment console for economy of space and ease of transportation.

SUMMARY

The present invention advantageously provides a method and system for the recovery of expanded refrigerant from a cryotreatment system for storage and disposal. A medical system may include: a refrigerant recovery circuit, the refrigerant recovery circuit including: a first fluid flow path having: a first compressor; and a fluid recovery reservoir, the first fluid flow path including a primary refrigerant; and a closed-loop second fluid flow path including: a thermal exchange device that is in thermal communication with the fluid recovery reservoir; a second compressor; and a condenser, the closed-loop second fluid flow path including a secondary refrigerant (for example, AZ20). The system may be configured to be in fluid communication with a medical facility. The refrigerant recovery circuit may further comprise an insulating container in the first fluid flow path, and the fluid recovery reservoir and the thermal exchange device may both be located within the insulating container. The thermal exchange device may be coiled around at least a portion of the fluid recovery reservoir. The flow of the secondary refrigerant within the closed-loop second fluid flow path may reduce the temperature of the primary refrigerant. Further, the first compressor may compress the primary refrigerant to a pressure of approximately 100 psi. The system may further include a cryotreatment system in fluid communication with the refrigerant recovery circuit, the cryotreatment system including: a source of the primary refrigerant; a third fluid flow path downstream of the primary refrigerant and configured to be in fluid communication with and upstream of a cryotreatment device; and a fourth fluid flow path downstream of the third fluid flow path, the fourth fluid flow path being in fluid communication with and upstream of the refrigerant recovery circuit, the fourth fluid flow path configured to be in fluid communication with and downstream of the cryotreatment device. The refrigerant recovery circuit and the cryotreatment system may be located within a cryotreatment console. The fluid recovery reservoir may be configured to be removed from the cryotreatment console. The cryotreatment system may further include a three-way solenoid valve located within the fourth fluid flow path.

A system for the recovery of a cryotreatment refrigerant may generally include: a refrigerant recovery circuit, the refrigerant recovery circuit including: a first fluid flow path having: a first compressor; and a fluid recovery reservoir, the first fluid flow path including a primary refrigerant; and a closed-loop second fluid flow path including: a thermal exchange device that is in thermal communication with the fluid recovery reservoir; a second compressor; and a condenser, the closed-loop second fluid flow path including a secondary refrigerant; and a cryotreatment system in fluid communication with the refrigerant recovery circuit, the cryotreatment system including: a source of the primary refrigerant; a third fluid flow path downstream of the primary refrigerant source and configured to be in fluid communication with and upstream of a cryotreatment device; and a fourth fluid flow path downstream of the third fluid flow path, the fourth fluid flow path being in fluid communication with and upstream of the refrigerant recovery circuit, the fourth fluid flow path configured to be in fluid communication with and downstream of the cryotreatment device. The system may be configured to be in fluid communication with a medical facility. The fluid recovery reservoir and the thermal exchange device may both be located within an insulating container. The thermal exchange device may be coiled around at least a portion of the fluid recovery reservoir. The flow of the secondary refrigerant within the closed-loop second fluid flow path may reduce the temperature of the primary refrigerant. The first compressor may compress the primary refrigerant to a pressure of approximately 100 psi. The system may be located within a cryotreatment console, and the fluid recovery reservoir may be configured to be removed from the cryotreatment console.

A system for recovery of expanded cryotreatment refrigerant may generally include: a refrigerant recovery conduit, the refrigerant recovery conduit including: a first fluid flow path having: a first compressor; and a fluid recovery reservoir, the first fluid flow path including a cryotreatment refrigerant; and a closed-loop second fluid flow path including: a thermal exchange device that is in thermal communication with the fluid recovery reservoir; a second compressor; a condenser; and an insulating container, the closed-loop second fluid flow path including a secondary refrigerant; a cryotreatment device; and a cryotreatment system in fluid communication with the refrigerant recovery circuit and the cryotreatment device, the cryotreatment system including: a source of the cryotreatment refrigerant; a third fluid flow path between the cryotreatment refrigerant source and the cryotreatment device, the cryotreatment refrigerant expanding within the cryotreatment device; and a fourth fluid flow path between the cryotreatment device and the refrigerant recovery circuit, expanded cryotreatment refrigerant from the cryotreatment device passing through the fourth fluid flow path and into the refrigerant recovery circuit. The expanded cryotreatment refrigerant may be compressed by the first compressor to pressure of approximately 100 psi and the temperature of the compressed cryotreatment refrigerant may be reduced within the fluid recovery reservoir by the flow of the secondary refrigerant within the thermal exchange device, the fluid recovery reservoir and the thermal exchange device being located within the insulating container. Further, the refrigerant recovery circuit and the cryotreatment system may be located within a cryotreatment console, and the cryotreatment console may be in fluid communication with the cryotreatment device.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
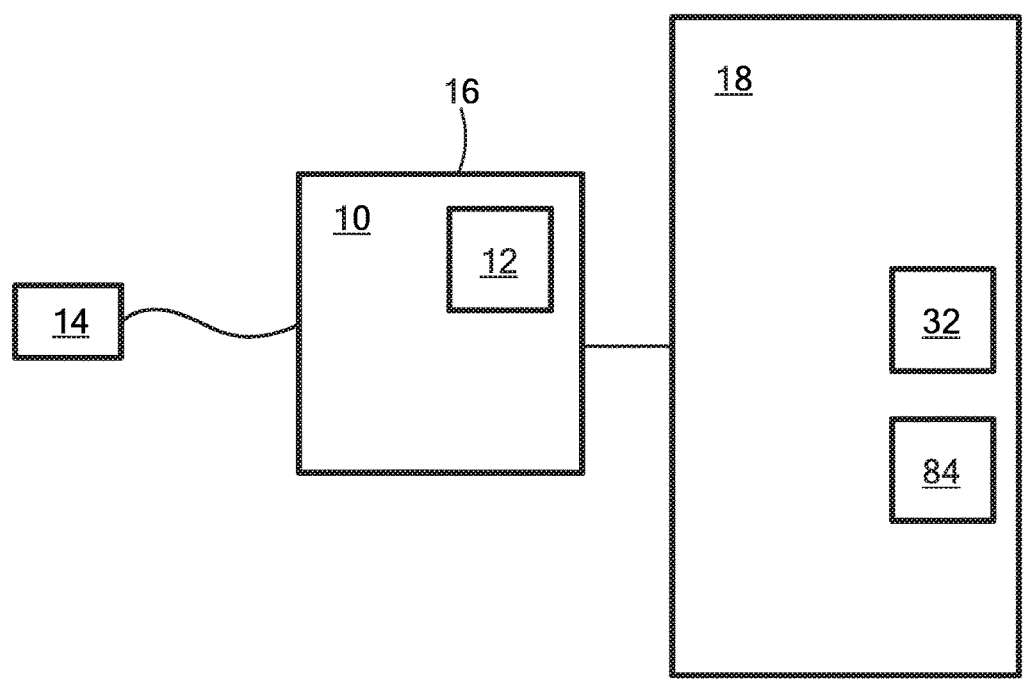
FIG. 1 shows a schematic view of an exemplary cryoablation system in communication with a medical facility, the cryoablation system including a refrigerant recovery circuit.

The present invention advantageously provides a method and system for the recovery of used refrigerant for reuse or disposal. Referring now to the drawing figures in which like reference designations refer to like elements, an exemplary schematic view of a cryotreatment system including a refrigerant recovery circuit in accordance with principles of the present invention is shown in FIG. 1. The cryotreatment system, generally designated as "10," may include a refrigerant recovery circuit 12 and may be in fluid, electrical, and mechanical communication with a cryotreatment device 14. The cryotreatment system 10 may be located entirely within a cryotreatment console 16. The cryotreatment console 16 may be in fluid communication with a scavenging or recovery system of a medical facility 18.

Figure 2:
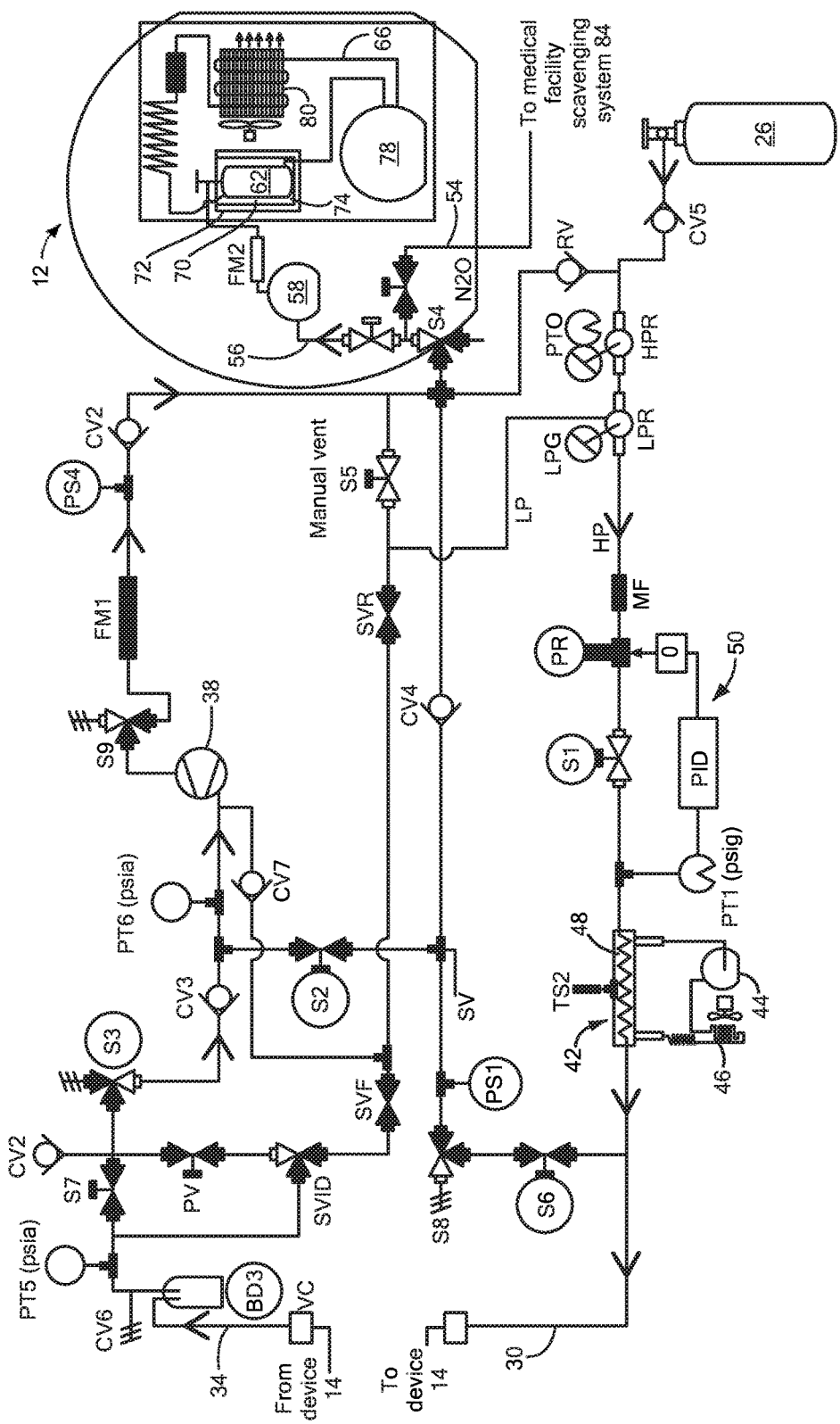
FIG. 2 shows a detailed schematic view of the exemplary cryoablation system including a refrigerant recovery circuit, expanded refrigerant vapor passing into the refrigerant recovery circuit.
Figure 3:
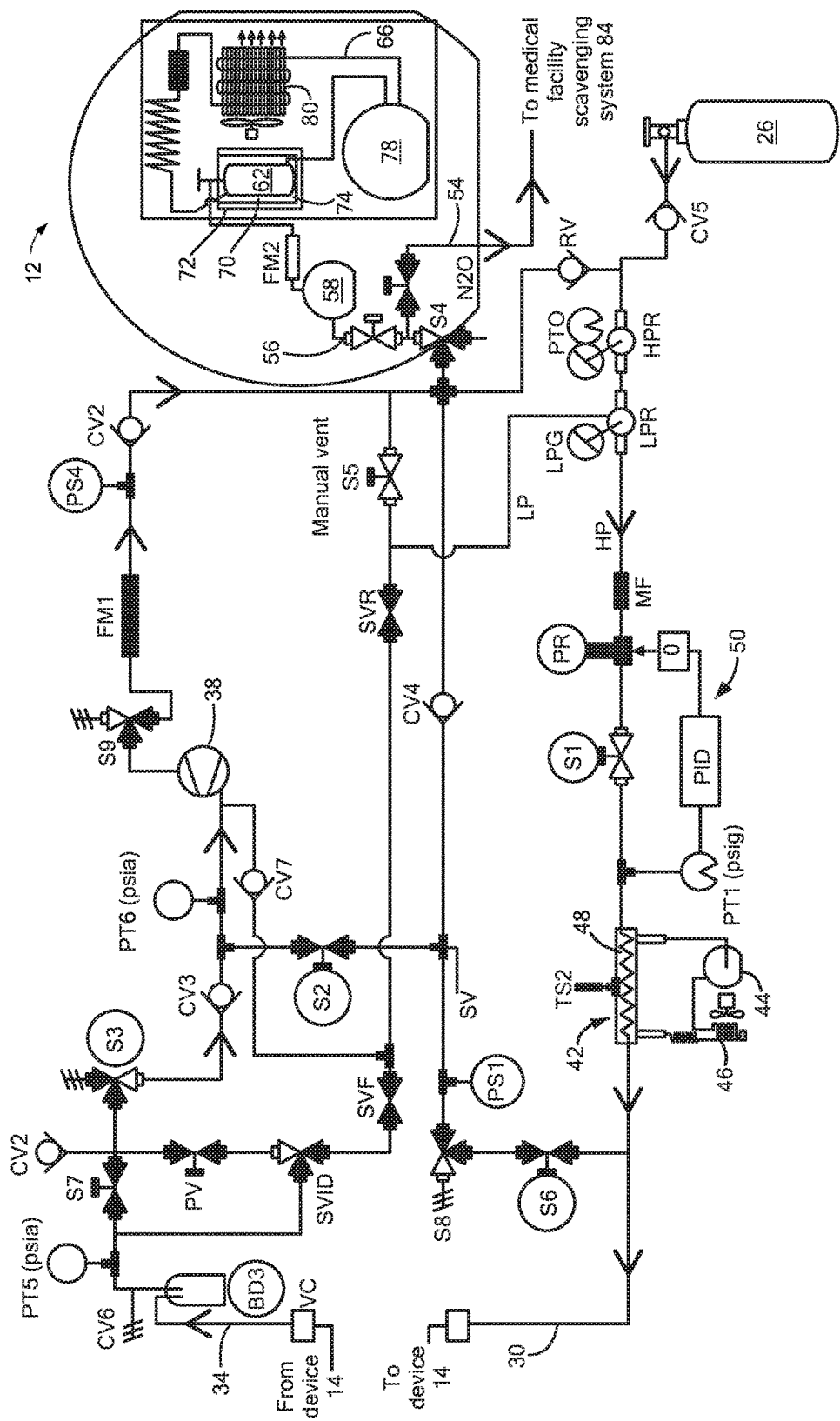
FIG. 3 shows a detailed schematic view of the exemplary cryoablation system including a refrigerant recovery circuit, expanded refrigerant vapor passing into a medical facility scavenging line.

Referring now to FIGS. 2 and 3, the cryotreatment system 10 may include one or more fluid supply reservoirs 26, such as pressurized tanks, that include a coolant, cryogenic refrigerant, or the like in fluid communication with a fluid delivery conduit 30 and the cryotreatment device 14. As a non-limiting example, the refrigerant may be nitrous oxide ($N_2O$), such as a native or in-facility, integrated source of nitrous oxide 32 in the medical facility 18, in which case the fluid supply reservoir 26 may be located external to the cryotreatment console 16. Additionally or alternatively, the fluid supply reservoir may be located within the console 16, and the native refrigerant from the medical facility 18 may not be used. The cryotreatment system 10 may include a fluid recovery conduit 34 in fluid communication with the cryotreatment device 14 and a recovery reservoir 62 of the refrigerant recovery circuit 12, which is described in more detail below.

The cryotreatment system 10 may also include a vacuum pump 38 for creating a pressure gradient to draw expanded (used) refrigerant from the cryotreatment device 14, into the fluid recovery conduit 34 and then into the refrigerant recovery circuit 12. The system's fluid flow path may include at least the fluid delivery conduit 30 and the fluid recovery conduit 34, in addition to various other conduits and/or secondary flow paths. The cryotreatment system 10 may also include pumps, valves, controllers or the like to recover and/or re-circulate fluid delivered to the handle, the elongate body, and/or the fluid pathways of the cryotreatment device 14, as described in more detail below.

The cryotreatment system 10 may include one or more controllers, processors, and/or software modules containing instructions or algorithms to provide for the automated operation and performance of the features, sequences, or procedures described herein. For example, the cryotreatment system 10 may include one or more computers that include one or more processors for receiving signals from one or more sensors throughout the system 10, and or for the automatic, semi-automatic, and/or manual operation of the system 10. The one or more computers may include one or more user input devices by which a user can program system parameters such as the inflation and deflation of one or more balloons of the cryotreatment device 14, circulation of refrigerant through the fluid delivery 30 and recovery 34 conduits, and/or the operation of one or more electrodes or other thermal delivery elements. The user input devices may include keyboards, knobs, buttons, dials, foot pedals, mice, touchscreens, voice input units, and/or switches. Additionally, the user may use the user input devices to override the automatic operation of the system 10 either programmed into or predetermined by the cryotreatment system 10. Still further, signals received by the one or more processors may be used to automatically or semi-automatically control the cryotreatment device 14 and/or the circulation of refrigerant therein. The one or more computers may further include one or more displays, such as computer screens or other visual elements in communication with the one or more processors and/or user input devices. Finally, the cryotreatment system 10 may include one or more speakers or other audio alert generators that are in communication with the one or more processors and/or the user input devices.

The system 10 and/or the cryotreatment device 14 may further include one or more sensors to monitor the operating parameters throughout the system 10, including for example, pressure, temperature, flow rates, volume, or the like in the cryotreatment console 16 and/or the cryotreatment device 14, in addition to monitoring, recording or otherwise conveying measurements or conditions within the device 14 or the ambient environment at the distal portion of the device 14. The sensor(s) may be in communication with the cryotreatment console 16 for initiating or triggering one or more alerts or therapeutic delivery modifications during operation of the device 14. One or more valves, controllers, or the like may be in communication with the sensor(s) to provide for the controlled dispersion or circulation of fluid through the lumens/fluid paths of the device 14 and system 10. Such valves, controllers, or the like may be located in a portion of the cryotreatment device 14 and/or in the cryotreatment console 16.

While the cryotreatment device 14 may be in fluid communication with a fluid source to cryogenically treat selected tissue, it is also contemplated that the device 14 may additionally include one or more electrically conductive portions or electrodes thereon coupled to a radiofrequency generator or power source as a treatment or diagnostic mechanism.

As discussed above, the system fluid flow path may include one or more valves, conduits, secondary flow paths, one or more fluid supply reservoirs 26, one or more fluid recovery reservoirs 62, a vacuum pump 38, and other system components. The cryotreatment system 10 may also include one or more subcoolers 42 with various refrigeration components such as a compressor 44, condenser 46, capillary tube, thermoelectric elements, and/or thermal exchange device 48. A subcooler 42, such as that shown in FIG. 2, may be used to further cool the refrigerant as it passes within the fluid delivery conduit 30 from the fluid supply reservoir 26 to the cryotreatment device 14. The fluid delivery conduit and other fluid flow paths between the fluid supply reservoir 26 and the device 14 may further include a PID circuit 50 and one or more valves and/or other components (for example, solenoid valves S1, S6, and S8, pressure transducer PT1, pressure relief valve PR, pressure switch PS1, shown in FIG. 2).

Figure 4:
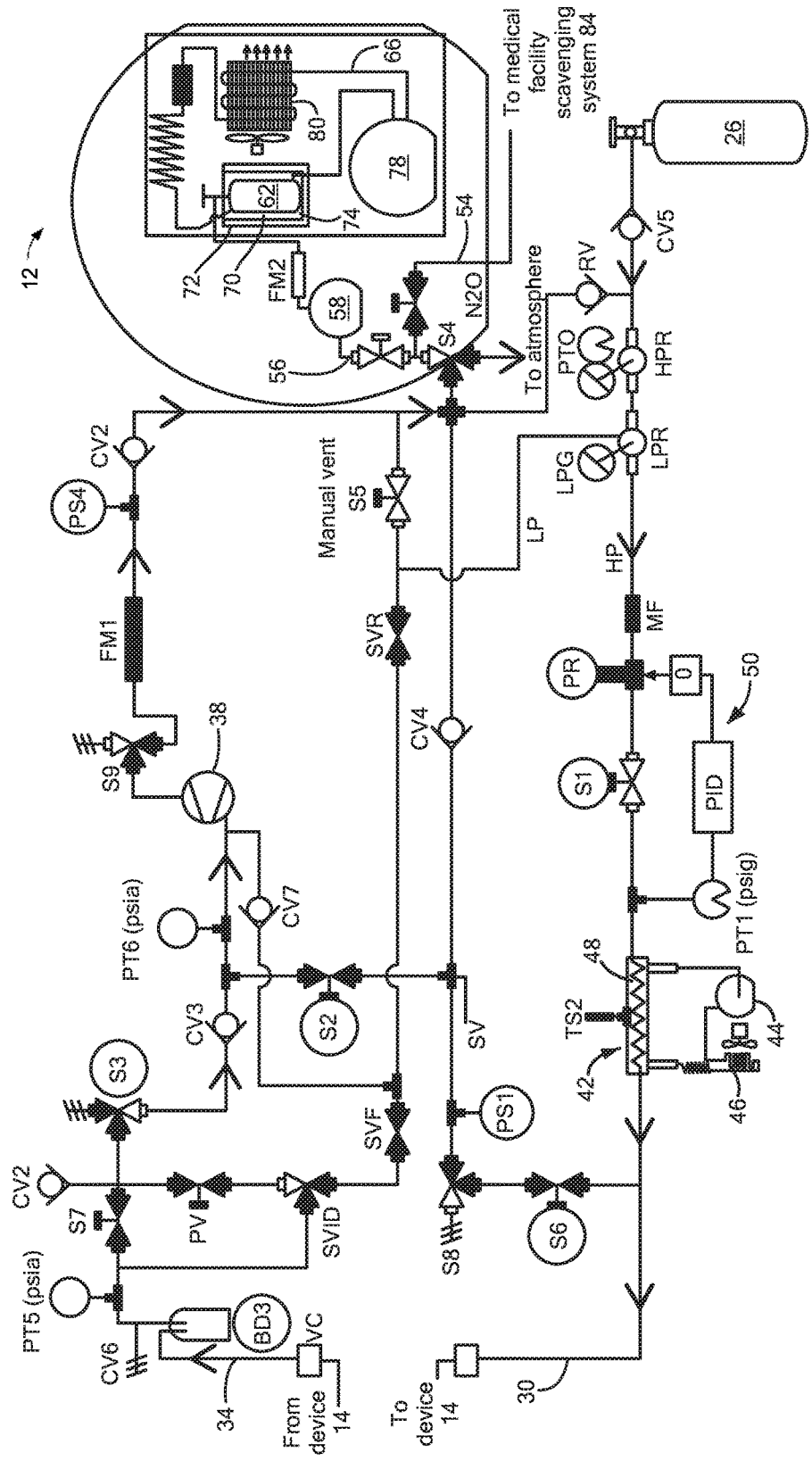
FIG. 4 shows a detailed schematic view of the exemplary cryoablation system including a refrigerant recovery circuit, expanded refrigerant vapor being vented to the atmosphere.

Expanded (used) refrigerant vapor from the cryotreatment device 14 may flow to the refrigerant recovery circuit 12 (as shown in FIG. 2), scavenged by the medical facility scavenging system (as shown in FIG. 3), and/or vented to the atmosphere (as shown in FIG. 4). Referring to FIG. 2, expanded refrigerant may, with the pressure gradient created by the vacuum 38, pass through the fluid recovery conduit 34 from the cryotreatment device 14, through check valve CV6, pressure transducer PT5, through three-way solenoid valve S9, through three-way solenoid valve S4, and into the refrigerant recovery circuit 12. As a non-limiting example, three-way solenoid valve S9 may vent air to the atmosphere when the system starts and air within the system is removed before beginning a cryoablation procedure. Once a cryoablation procedure begins, S9 may allow refrigerant to pass on to the refrigerant recovery circuit 12. As it enters the refrigerant recovery circuit 12 through a first flow path 56, the expanded refrigerant vapor may be at approximately 10 psig. After passing through a first compressor 58 of the refrigerant recovery circuit 12, however, the refrigerant vapor may be compressed to have a pressure of approximately 100 psi (±10 psi). After passing through the first compressor 58, the compressed refrigerant may pass into a fluid recovery reservoir 62 for temporary storage and later disposal. As a non-limiting example, the fluid recovery reservoir 62, or the insulating container and the fluid recovery reservoir 62, may be removed from the refrigerant recovery circuit 12 and disposed. The recovery reservoir 62 may be reusable after the recovered refrigerant is disposed, or the recovery reservoir 62 may be disposable and a new reservoir used as needed.

The refrigerant recovery circuit 12 may also include a second fluid flow path 66, which may contain a secondary refrigerant, such as AZ20. The secondary refrigerant may flow through a thermal exchange device 70 that is in a thermal exchange relationship (that is, in thermal communication) with the fluid recovery reservoir 62. As a non-limiting example, the thermal exchange device 70 may be an evaporator having a coiled configuration and may be wrapped one or more times about a circumference of the fluid recovery reservoir 62. Further, the recovery reservoir 62 and the thermal exchange device 70 may together be located within an insulating container 72. The insulating container 72 may be at least partially composed of a material or layers of materials that prevent or reduce the transmission of heat. Additionally, the insulating container 72 may be filled with, and the thermal exchange device 70 and the recovery reservoir 62 may be surrounded by, a nonfreezing liquid 74 such as methanol, propylene glycol, or other liquid having similar properties. The nonfreezing liquid 74 may improve heat transfer between the thermal exchange device 70 and the recovery reservoir 62. Thus, the flow of secondary refrigerant within the thermal exchange device 70 may cool the refrigerant within the recovery reservoir 62 and the insulating container 72 may improve cooling efficiency. The insulting container 72 may have a shape and configuration similar to that of the recovery reservoir 62, and may be sized just large enough to accommodate the recovery reservoir 62, thermal exchange device 70, and nonfreezing liquid 74 therein. Further, the recovery reservoir 62 optionally may be integrated within the insulating container 72. From the thermal exchange device 70, the secondary refrigerant may pass through a second compressor 78, then through a condenser 80, and then back into the thermal exchange device 70. The secondary refrigerant may also pass through a dryer and capillary tube or expansion device before passing into the thermal exchange device 70. Thus, the secondary refrigerant may be recycled through the second fluid flow path 66 to continue cooling the recovered refrigerant within the recovery reservoir 62.

Additionally or alternatively, at least a portion of the expanded refrigerant may be scavenged by the native scavenging system 84 within the medical facility 18 (as shown in FIG. 3). In this case, the expanded refrigerant vapor may, with the pressure gradient created by the vacuum 38, pass through the fluid recovery conduit 34 from the device 14, through check valve CV6, pressure transducer PT5, through three-way solenoid valve S9, through three-way solenoid valve S4, and into the medical facility scavenging line 54. As shown in FIG. 4, the expanded refrigerant vapor may also pass through one or more additional valves, transducers, and system components. This fluid flow path may be used if, for example, the refrigerant recovery circuit 12 malfunctions or if the refrigerant recovery reservoir 62 is full.

Additionally or alternatively, at least a portion of the expanded refrigerant vapor may be vented to the atmosphere (as shown in FIG. 4). In this case, expanded refrigerant may, with the pressure gradient created by the vacuum 38, pass through the fluid recovery conduit 34 from the device 14, through check valve CV6, pressure transducer PT5, through three-way solenoid valve S9, and through three-way solenoid valve S4, from where the vapor is vented to the atmosphere. This fluid flow path may be used when the system (for example, pressure switch PS4) detects a high pressure in the refrigerant recovery circuit 12 and/or the medical facility scavenging system 84.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system for recovery of expanded cryotreatment refrigerant for use with a scavenging system separate from the system, the system comprising:
   a cryotreatment device;
   a fluid recovery conduit in communication with the cryotreatment device, the fluid recovery conduit being in further communication with one of a scavenging line connectable to the scavenging system and a console, the console having a refrigerant recovery circuit, the refrigerant recovery circuit including:
   a first fluid flow path having:
      a first compressor; and
      a fluid supply reservoir,
      the first fluid flow path including a cryotreatment refrigerant;
   a closed-loop second fluid flow path configured to cool the cryotreatment refrigerant including:
      a first thermal exchange device that is in direct thermal communication with the fluid supply reservoir;
      a second compressor;
      a condenser; and
      an insulating container containing a nonfreezing liquid,
      the closed-loop second fluid flow path including a secondary refrigerant; and
   a closed-loop third fluid flow path configured to cool the cryotreatment refrigerant including:
      a removable fluid recovery reservoir configured to retain the cryotreatment refrigerant;
      a second thermal exchange device that is disposed around the removable fluid recovery reservoir and is in a direct thermal exchange relationship with the removable fluid recovery reservoir;
      a third refrigerant; and
   a cryotreatment system in fluid communication with the refrigerant recovery circuit and the cryotreatment device, the cryotreatment system including:
      a cryotreatment refrigerant source;
      the closed-loop third fluid flow path being between the cryotreatment refrigerant source and the cryotreatment device, the cryotreatment refrigerant expanding within the cryotreatment device; and
      a fourth fluid flow path between the cryotreatment device and the refrigerant recovery circuit, expanded cryotreatment refrigerant from the cryotreatment device passing through the fourth fluid flow path and into the refrigerant recovery circuit,
   the expanded cryotreatment refrigerant being compressed by the first compressor to pressure of approximately 100 psi and a temperature of the compressed cryotreatment refrigerant being reduced within the removable fluid recovery reservoir by the flow of the third refrigerant within the second thermal exchange device, the removable fluid recovery reservoir and the second thermal exchange device being surrounded by the nonfreezing liquid, the cryotreatment refrigerant flowing within the removable fluid recovery reservoir where the second thermal exchange device cools the cryotreatment refrigerant,
   the refrigerant recovery circuit and the cryotreatment system being located within a cryotreatment console, the cryotreatment console being in fluid communication with the cryotreatment device; and
   the first fluid flow path being further configured to direct refrigerant towards the scavenging line of the scavenging system when at least one of:
      the refrigerant recovery circuit malfunctions; and
      the removable fluid recovery reservoir is full.

* * * * *